United States Patent [19]

Okamoto

[11] Patent Number: 4,710,273

[45] Date of Patent: Dec. 1, 1987

[54] OLEFIN PURIFICATION PROCESS

[75] Inventor: Ted T. Okamoto, Baton Rouge, La.

[73] Assignee: Ethyl Corporation, Richmond, Va.

[21] Appl. No.: 763,525

[22] Filed: Aug. 8, 1985

[51] Int. Cl.⁴ .................... B01D 3/34; C07C 7/148
[52] U.S. Cl. ........................ 203/29; 203/38;
   208/49; 252/45; 568/18; 585/800; 585/811;
   585/856
[58] Field of Search ........... 203/29, 38, 39; 252/45,
   252/48.8; 585/856, 853, 836, 800, 811; 208/49,
   46; 568/18

[56] References Cited

U.S. PATENT DOCUMENTS

| | | | |
|---|---|---|---|
| 2,386,773 | 10/1945 | Badertscher et al. | 585/856 |
| 2,640,804 | 6/1953 | Whitney | 203/29 |
| 2,708,199 | 5/1955 | Eby | 252/45 |
| 3,471,404 | 10/1969 | Myers | 252/45 |
| 3,655,520 | 4/1972 | Harkins | 203/38 |
| 3,860,528 | 1/1975 | Dewitt et al. | 585/856 |
| 3,864,420 | 2/1975 | Dombro | 585/856 |
| 4,194,980 | 3/1980 | Braid | 252/45 |
| 4,225,488 | 9/1980 | Horodysky et al. | 252/45 |
| 4,240,958 | 12/1980 | Braid | 252/45 |
| 4,450,069 | 5/1984 | Kidwell et al. | 585/856 |
| 4,511,753 | 4/1985 | Smith et al. | 585/856 |

OTHER PUBLICATIONS

Smalheer et al: *Lubricant Additives*, pp. 9–11 (1967).

*Primary Examiner*—Wilbur Bascomb
*Attorney, Agent, or Firm*—Donald L. Johnson; John F. Sieberth; J. D. Odenweller

[57] ABSTRACT

Olefin mixtures containing vinyl, vinylidene and internal olefins are upgraded in value by removing the vinylidene olefin content and lowering the internal olefin content by selective reaction with a sulfur halide such as $S_2Cl_2$ followed by reaction with aqueous alkali metal hydrosulfide and optionally alkali metal sulfide. The reaction mixture is distilled to remove mainly vinyl and a reduced amount of internal olefins. The distillation residue is an effective extreme pressure additive for lubricating oil.

12 Claims, No Drawings

OLEFIN PURIFICATION PROCESS

BACKGROUND OF THE INVENTION

Olefin mixtures containing vinyl, vinylidene and internal olefins of similar carbon number are difficult to separate by distillation based solely on the olefin type because vinyl, vinylidene and internal olefins having the same carbon number boil very close together This is generally the case when the olefins are made by a process capable of producing all three types of olefins. For example, the ethylene chain growth process using triethylaluminum followed by olefin displacement as practiced commercially can produce olefins containing from 4 up to 30 or more carbon atoms. The olefin type is mainly vinyl olefins, i.e. $R-CH=CH_2$ wherein R is an aliphatic hydrocarbon group, but can contain lesser amounts of internal olefins, i.e. $R-CH=CH-R$ wherein R is an aliphatic hydrocarbon group and vinylidene olefins, i.e.

wherein R and R' are aliphatic hydrocarbon groups. When practiced to produce olefin mixtures containing up to 12 carbon atoms, the mixtures are predominantly, i.e. about 80 mole percent or more vinyl olefins. However when practiced to produce higher olefins, e.g. containing 14 or more carbon atoms, the amount of internal olefins and especially vinylidene olefins increases sharply such that in the $C_{16-18}$ olefin range the olefin mixture will contain about 25–35 mole percent vinylidene olefins and 5–10 mole percent internal olefins. In some uses the vinylidene olefin content of olefin mixtures is not detrimental. However in some uses, the presence of vinylidene olefin decreases the value of the olefin mixture. For example, detergents can be made by reacting olefin mixtures with hydrogen sulfide to add hydrogen sulfide to the double bond forming a mercaptan. These in turn can be oxidized to form sulfonic acids which when converted to their salts are effective detergents. However vinylidene olefins react with hydrogen sulfide to form tertiary mercaptans which are very difficult to oxidize to sulfonic acids. Thus a need exists for a process for separating vinylidene olefins from a mixture containing vinyl, vinylidene and internal olefins which mixtures cannot be readily separated by distillation.

SUMMARY OF THE INVENTION

It has now been discovered that olefin mixtures containing vinyl, vinylidene and internal olefins can be upgraded by lowering the vinylidene olefin content by reacting the mixture with a sulfur halide to selectively sulfur-bridge the vinylidene and internal olefins followed by reaction of the mixture with an aqueous alkali metal hydrosulfide and optionally alkali metal sulfide to react with any halogen substituents formed. This treatment has also been found to lower the amount of internal olefins which still further improves the quality of final product. The final reaction product can be separated by distilling the vinyl and internal olefins leaving the sulfur-bridged vinylidene olefin and at least some sulfur-bridged internal olefin products in the distillation residue. This residue is a very effective extreme pressure (EP) additive in lubricating and cutting oils and functions to inhibit metal to metal weld and score in sliding metal surfaces under high pressure such as in gears and machine tools.

DESCRIPTION OF THE PREFERRED EMBODIMENTS

A preferred embodiment of the invention is a process for removing vinylidene olefins from a mixture of $C_6-C_{30}$ olefins containing about 5–40 mole percent vinylidene olefins, 0–20 mole percent internal olefins and the balance vinyl olefins said process comprising:

(A) reacting said mixture of olefins with a sulfur halide in the presence of a Lewis Acid catalyst to selectively couple said vinylidene olefins through a sulfide or polysulfide bridge to form an intermediate mixture containing chloro-substituted sulfide-bridged compounds, (B) reacting said intermediate with an aqueous alkali metal hydrosulfide solution to form a second intermediate mixture and (C) distilling said vinyl olefins and internal olefins from said second intermediate mixture to obtain as the distillate an olefin mixture containing substantially less vinylidene and internal olefins than were in said mixture of $C_6-C_{30}$ olefins and leaving as the distillation residue a sulfur-containing product useful as an extreme pressure additive for lubricating oil.

The process is useful to remove both vinylidene and internal olefins from any mixture of olefins which contains vinylidene and internal olefins. It is most useful in removing vinylidene olefins from olefin mixtures made by the Ziegler Process of ethylene chain growth on triethylaluminum followed by olefin displacement. Such olefin products contain about 4 to 30 or more carbon atoms depending on reaction conditions. When used to make olefin containing 12 or less carbon atoms the products are predominantly (i.e. over 80 mole percent) linear vinyl olefins and contain lesser amounts of vinylidene and internal As used herein olefins are classified as:

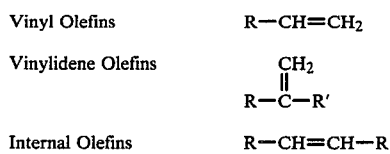

wherein R and R' are alkyl groups.

When the Ziegler Process is used to make higher olefins, the amount of internal and vinylidene olefins increases and also more chain branching occurs. In general the present process can be used to upgrade an olefin mixture wherein the olefins contain about 6–30 carbon atoms of which about 5–40 mole percent are vinylidene, about 0–20 mole percent are internal and the balance are vinyl olefins. More often the olefin mixtures will contain at least some internal olefins and have the composition of about 5–40 mole percent vinylidene, about 3–20 mole percent internal and the balance vinyl olefins.

The mixture of olefins is first reacted with a sulfur halide such as $SBr_2$, $SCl_2$, $S_2Br_2$, $S_2Cl_2$ and the like. Preferably the sulfur halide is sulfur monochloride, $S_2Cl_2$. The reaction is conducted in the presence of a Lewis Acid catalyst such as $AlCl_3$, $AlBr_3$, $BF_3$, $BCl_3$, $FeCl_3$, $SnCl_4$, $ZnCl_2$, $GaCl_3$, $ZnBr_2$ and the like. The preferred catalyst are $FeCl_3$ and $AlCl_3$, most preferably FeCl$_3$. The amount of Lewis Acid catalyst is a catalytic amount. In general this is about 0.1–5.0 weight percent, more preferably about 0.3–0.6 weight percent of the olefin mixture.

A preferred mode of carrying out the process is to mix the olefin and Lewis Acid catalyst in a reaction vessel at a very fairly low temperature to avoid isomerization, e.g. under 50° C. more preferably about 10°–40° C., and then add the sulfur halide slowly while controlling the temperature to prevent extensive isomerization. A useful addition temperature is initially about 10°–30° C. rising to 40°–50° C. during the sulfur halide addition.

The amount of sulfur halide can vary over a wide range but should be sufficient to form a thio or polythio bridge between most of the vinylidene olefins. This is shown in the following equation:

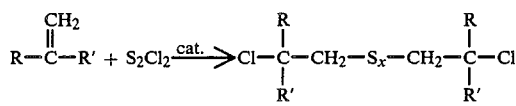

wherein R and R' are aliphatic hydrocarbon groups and x is an integer of 1–3, generally 2. A useful range is about 0.5–1.0 moles of S$_2$Cl$_2$ per mole of vinylidene olefins in the olefin mixture. A more preferred range is about 0.5–0.9 and a still more preferred range is about 0.5–0.7 moles of S$_2$Cl$_2$ per mole of vinylidene olefin.

If the olefin mixture also contains internal olefins and it is desired to lower the amount of internal olefins then the amount of sulfur halide should be increased to provide an amount needed to sulfur bridge the internal olefins. For example the amount can be increased to provide about 0.5–1.0 moles of S$_2$Cl$_2$ per each mole of vinylidene and internal olefin.

The addition of the sulfur halide is usually completed in about 0.5–8 hours depending upon scale and cooling capacity. Following the addition, the mixture can be stirred at about 40°–50° C. for a short period (e.g. 0.5–1 hour) to assure completion of the vinylidene sulfur coupling.

In the next stage, the intermediate from the first stage is reacted with an aqueous solution of an alkali metal hydrosulfide, e.g. NaSH, KSH, etc., most preferably NaSH. Alternatively the first intermediate can be reacted with an equal mole aqueous mixture of NaOH and H$_2$S or of Na$_2$S and H$_2$S which form NaSH in situ. The amount of alkali metal hydrosulfide should be an amount sufficient to react with the halogens bonded to the first intermediate and any unreacted sulfur halide. A useful range is about 1–2 moles of NaSH per each 0.5–0.9 moles of sulfur halide (e.g. S$_2$Cl$_2$) used in the first stage. A more preferred range is about 1–1.5 moles of NaSH per each mole of S$_2$Cl$_2$.

It is beneficial but not essential to include Na$_2$S in the aqueous NaSH solution. Thus the amount of Na$_2$S can range from none up to about 0.25 moles for each 0.5–0.9 moles of sulfur halide (e.g. S$_2$Cl$_2$). A more preferred amount of Na$_2$S is about 0.1–0.5 moles per mole of S$_2$Cl$_2$.

The amount of water should be an amount sufficient to dissolve the NaSH and Na$_2$S used in the second stage. A useful range is about 120–200 parts by weight water for each 100 parts of NaSH and Na$_2$S.

The EP properties of the residual product following distillation are improved by including a lower alcohol in the aqueous NaSH-Na$_2$S solution. These include methanol, ethanol, n-propanol, isopropanol, isobutanol and the like. The more preferred alcohols are ethanol, isopropanol and mixtures thereof. The amount of alcohol can range from none up to about 200 parts by weight for each 100 parts of water. A preferred ranqe is about 75–150 parts of alcohol for each 100 parts of water.

The second stage is conducted by adding the first stage intermediate to the aqueous NaSH and optionally Na$_2$S solution or by adding the aqueous solution to the first stage intermediate. The resulting mixture is then stirred at an elevated temperature for a time sufficient to react all or substantially all of the chlorine. This usually requires about 0.5–8 hours at a temperature of 70° C. up to reflux, more preferably 80° C. up to reflux.

The second stage reaction mixture is then allowed to separate into two phases. The lower aqueous phase is removed. The upper organic phase can then be stirred with aqueous NaOH to reduce chloride content although this step is not necessary. When this step is concluded the aqueous caustic usually contains about 5–20 weight percent NaOH and the mixture of aqueous causticorganic phase are stirred at a temperature of about 20°–70° C. for about 0.5–1 hour.

The organic phase, whether treated with aqueous caustic or not is water washed to remove salts, alcohols and other water-soluble products. The washed organic phase is then distilled to remove an olefin distillate which consist mainly of vinyl olefins and a small amount of internal olefins and a greatly reduced amount of vinylidene olefins. Most of the vinylidene olefins and at least part, e.g. 5–90 mole percent, of the internal olefins have been coupled by sulfur bridging during the process to form oligomers containing two or more vinylidene and/or internal olefin derived units. These are high boiling high molecular weight oligomers and remain as the distillation residue. The distillation can be conducted until substantially all of the vinyl olefins are distilled out. The distillation can be started at atmospheric pressure but is preferably completed at reduced pressure as shown in the examples.

The distillate will be mainly vinyl olefins containing some internal olefins and very little vinylidene olefins. The actual composition will depend somewhat on the composition of the starting olefin mixture and amount of sulfur halide used but typically with an initial olefin mixture of about 60–80 mole percent vinyl, 25–35 mole percent vinylidene and 3–10 mole percent internal olefin, the final distillate will consist of about 90–98 mole percent vinyl olefins, 2–5 mole percent internal olefins and less than 3 mole percent vinylidene olefins.

The following examples show how the process can be carried out.

EXAMPLE 1

In a glass reaction vessel was placed 137 grams of a C$_{16}$ olefin mixture consisting essentially of 71.6 mole percent vinyl olefin, 7.5 mole percent internal olefin and 20.9 mole percent vinylidene olefin. To this was added 0.2 grams of aluminum chloride and the mixture stirred under nitrogen. Following this 8.4 grams of S$_2$Cl$_2$ was added dropwise at a rate which maintained a 40° C. reaction temperature. Stirring was continued 30 minutes at 40° C. and then a solution consisting of 10.2 grams of NaSH 2H$_2$O, 10 ml water, 10 ml ethanol and 15 ml isopropanol was added and the mixture stirred at 95° C. for 1 hour. Stirring was stopped and the phases separated. The lower aqueous phase was removed and the upper organic phase was washed twice with water. The organic phase was then distilled to remove volatile olefins up to a liquid temperature of 140° C. at 0.4 mm Hg. The distillate analyzed 88.6 mole percent vinyl olefin, 8.1 mole percent internal olefin and 3.3 mole percent vinylidene olefin. The distillation bottoms represented 37 weight percent of the reaction mixture and had a molecular weight of about 600 and contained 8 weight percent sulfur.

EXAMPLE 2

In a glass reaction vessel was placed 500 grams of a mixture of $C_{16}$ and $C_{18}$ olefins analyzing 64.9 mole percent vinyl olefins, 6.9 mole percent internal olefins and 28.2 mole percent vinylidene olefins. To this was added 4.5 grams of ferric chloride and the mixture stirred while adding 60 grams of $S_2Cl_2$ dropwise at a rate which maintained a reaction temperature of about 40° C. Stirring was then continued at 40° C. for 10 minutes and then a solution of 50 grams NaSH 2$H_2O$, 10 grams $Na_2S$, 100 grams water, 39 grams ethanol and 78 grams isopropanol were added and the mixture stirred at 80° C. for 1 hour. Stirring was stopped and the phases separated. The lower aqueous phase (291.3 grams) was removed and the organic phase was washed twice with 100 gram portions of water at 40° C. The washed organic phase was distilled under vacuum to a final bottoms liquid temperature of 160° C. at 0.4 mm Hg to recover 259.6 grams of distillate analyzing 95.0 mole percent vinyl olefin, 4.3 mole percent internal olefin and only 0.7 mole percent vinylidene olefin. The distillation residue (280.2 grams) analyzed 9.8 weight percent sulfur and 4.8 weight percent chlorine.

The distillation residue is useful as an extreme pressure additive for lubricating oil, especially those used under extreme pressure conditions such as gear oils and cutting oils. The amount of the residue used as an additive can vary over a wide range from about 0.1 to about 10 weight percent or more of the oil composition. Other EP additives can be included such as sulfurized isobutylene to supplement the properties of the present additive can be included. Likewise other additives such as antioxidants; mono, di and trialkyl phosphites; metal deactivators: $P_2S_5$-olefin reaction products; zinc dialkyl dithiophosphate, calcium alkaryl sulfonates, barium phosphonates and the like.

I claim:

1. A process for removing vinyldene olefins from a mixture of $C_6$–$C_{30}$ olefins containing about 5–40 mole percent vinylidene olefins, 0–20 mole percent interval olefins and the balance vinyl olefins said process comprising:
   (A) reacting said mixture of olefins with a sulfur halide in the presence of a Lewis Acid catalyst to selectively couple said vinylidene olefins through a sulfide or polysulfide bridge to form an intermediate mixture containing halo-substituted sulfide-bridged compounds,
   (B) reacting said intermediate mixture with an aqueous alkali metal hydrosulfide solution to form a second intermediate mixture and
   (C) distilling said vinyl olefins and internal olefins from said second intermediate mixture to obtain as the distillate an olefin mixture containing substantially less vinylidene olefins than were in said mixture of $C_6$–$C_{30}$ olefins and leaving a residual product useful as an extreme pressure additive for lubricating oil.

2. A process of claim 1 wherein said sulfur halide is sulfur monochloride, $S_2Cl_2$.

3. A process of claim 2 wherein said alkali metal hydrosulide is sodium hydrosulfide.

4. A process of claim 3 wherein said Lewis Acid is selected form aluminum chloride, ferric chloride, boron trifluoride and boron trichloride.

5. A process of claim 4 wherein step (B) is conducted in the additional presence of a lower water-soluble alcohol.

6. A process of claim 5 wherein said alcohol is isopropanol.

7. A process of claim 4 wherein said Lewis Acid catalyst is ferric chloride.

8. A process of claim 7 wherein step (B) is conducted in the additional presence of a lower water-soluble alcohol.

9. A process of claim 8 wherein said alcohol is isopropanol.

10. A process for removing vinylidene olefins from a mixture of $C_6$–$C_{30}$ olefins which contains about 5–40 mole percent vinylidene olefins, 3–20 mole percent internal olefins and the balance vinyl olefins said process comprising:
    (A) reacting said mixture of olefins with about 0.5–0.9 moles of $S_2Cl_2$ per mole of said vinylidene and internal olefins in the presence of a Lewis Acid catalyst to selectively couple said vinylidene and internal olefins through a sulfide or polysulfide bridge forming a first intermediate mixture,
    (B) reacting said first intermediate mixture with a solution of about 1–2 moles of NaSH and 0–0.25 moles of $Na_2S$ per mole of $S_2Cl_2$, said solution containing about 25–50 weight percent water and about 25–60 weight percent lower water-soluble alcohol to form a second intermediate mixture.
    (C) washing said second intermediate mixture with water to remove alcohol, NaCl and other water-soluble materials, and
    (D) distilling said second intermediate mixture to recover an olefin distillate which contains substantially less vinylidene and internal olefin than were present in the initial olefin mixture.

11. A process of claim 10 wherein said Lewis Acid catalyst is aluminum chloride or ferric chloride.

12. A process of claim 11 wherein said lower water-soluble alcohol is selected from ethanol, isopropanol and mixtures thereof.

* * * * *

UNITED STATES PATENT AND TRADEMARK OFFICE
CERTIFICATE OF CORRECTION

PATENT NO. : 4,710,273

DATED : DECEMBER 1, 1987

INVENTOR(S) : TED T. OKAMOTO

It is certified that error appears in the above-identified patent and that said Letters Patent is hereby corrected as shown below:

Column 2, line 39 reads "and internal" and should read -- and internal olefins. -- .

Column 4, line 4 reads "ranqe" and should read -- range -- .

Column 4, line 23 reads "causticorganic" and should read -- caustic-organic -- .

Column 5, line 43 reads "additive can be included." and should read -- additive. -- .

Column 5, line 43 reads "other additives such" and should read -- other additives can be included such -- .

Column 5, line 44 reads "deactivators:" and should read -- deactivators; -- .

Column 5, line 51 reads "percent interval olefins" and should read -- percent internal olefins -- . (Compare Claim 1, page 10, line 3)

Column 6, line 14 reads "metal hydrosulide" and should read -- metal hydrosulfide -- .

UNITED STATES PATENT AND TRADEMARK OFFICE
CERTIFICATE OF CORRECTION

PATENT NO. : 4,710,273

DATED : DECEMBER 1, 1987

INVENTOR(S) : TED T. OKAMOTO

It is certified that error appears in the above-identified patent and that said Letters Patent is hereby corrected as shown below:

Column 6, line 52 reads "internal olefin" and should read -- internal olefins -- .

Signed and Sealed this

Twenty-fourth Day of May, 1988

Attest:

Attesting Officer

DONALD J. QUIGG

Commissioner of Patents and Trademarks